United States Patent [19]

Pankau

[11] 4,344,432
[45] Aug. 17, 1982

[54] DEVICE FOR COLLECTING BODY FLUIDS
[75] Inventor: Edward F. Pankau, Park Ridge, Ill.
[73] Assignee: The Kendall Company, Boston, Mass.
[21] Appl. No.: 223,186
[22] Filed: Jan. 7, 1981
[51] Int. Cl.³ .............................................. A61F 5/44
[52] U.S. Cl. ................................... 128/275; 128/295; 128/272.1
[58] Field of Search ............... 128/295, 272, 272.1, 128/294, DIG. 24

[56] References Cited
U.S. PATENT DOCUMENTS

| 4,085,751 | 4/1978 | Dodge | 128/275 |
| 4,085,755 | 4/1978 | Burrage | 128/272 |
| 4,116,227 | 9/1978 | Eisenberg et al. | 128/275 |
| 4,234,095 | 11/1980 | Safianoff | 128/272 |

Primary Examiner—Richard J. Apley
Assistant Examiner—T. J. Wallen
Attorney, Agent, or Firm—Powell L. Sprunger

[57] ABSTRACT

A device for collecting body fluids from a patient comprising, a receptacle having a chamber to receive the body fluids. The device has a conduit having a portion located in the chamber, with the conduit having a lumen extending along the conduit and an inflation opening communicating with the lumen. The device has an inflatable balloon of elastic material secured to the conduit in the chamber and defining a cavity communicating with the inflation opening, with the balloon comprising a material slightly permeable to liquid.

18 Claims, 3 Drawing Figures

DEVICE FOR COLLECTING BODY FLUIDS

BACKGROUND OF THE INVENTION

The present invention relates to devices for collecting body fluids from a patient.

Before the present invention, a number of collection bags have been proposed to receive urine from a patient. A catheter is placed in the patient such that it communicates with the patient's bladder, and during catheterization urine drains from the bladder through the catheter and a drainage tube to the collection bag for retention therein. Such systems should be closed to the atmosphere to minimize the possibility of contamination. Nonetheless, a persistent problem has been found in that the collected urine in the bag may become contaminated, resulting in possible undesired retrograde bacteria movement through the system to the bladder of the patient.

SUMMARY OF THE INVENTION

A principal feature of the present invention is the provision of an improved device for collecting body fluids from a patient.

The device comprises, a receptacle having a chamber to receive the body fluids. The device has a conduit having a portion located in the chamber, with the conduit having a lumen extending along the conduit and an inflation opening communicating with the lumen. The device has an inflatable balloon of elastic material secured to the conduit in the chamber and defining a cavity communicating with the inflation opening.

A feature of the present invention is that in one form the balloon comprises a material which is slightly permeable to liquid.

Another feature of the invention is that the balloon may be inflated with an antiseptic agent through the conduit.

Yet another feature of the invention is that the antiseptic agent diffuses through the permeable balloon over a period of time.

Still another feature of the invention is that the diffused antiseptic agent mixes with the collected body fluids.

Another feature of the invention is that the antiseptic agent introduced into the collected body fluids minimizes the possibility of bacterial growth in the body fluids.

Further features will become more fully apparent in the following description of the embodiments of this invention and from the appended claims.

DESCRIPTION OF THE PREFERRED EMBODIMENTS

Figure 1:
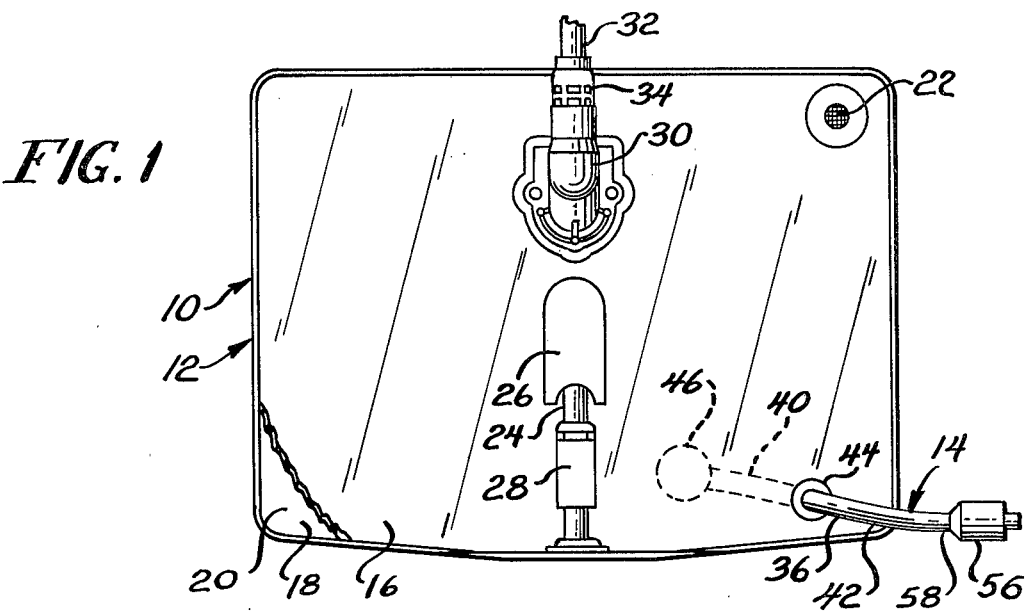
FIG. 1 is a fragmentary plan view, partly broken away, of a collection device of the present invention.
Figure 2:
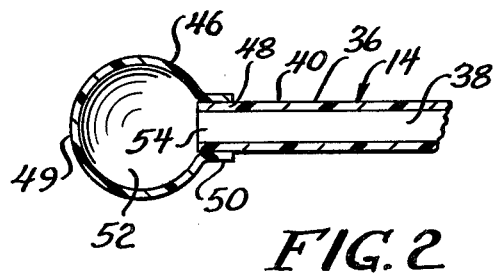
FIG. 2 is a fragmentary sectional view of a diffusion device for the collection device of FIG. 1.

Referring now to FIGS. 1-2, there is shown a device generally designated 10 for collecting body fluids comprising a receptacle or container 12 and a diffusion device 14. The container 12 has a front wall 16 and a back wall 18 of suitable flexible plastic material joined together at the edges of the front and back walls 16 and 18 to define a chamber 20 in the container 12. The container 12 may have a vent 22 with a bacteria filter of known type to filter bacteria passing from the atmosphere into the container chamber 20. The container 12 may have a tubular section 24 attached to a lower portion of the container front wall 16 and communicating with the chamber 20, with an outer end of the tubular section 24 being received in a pocket 26 on the front wall 16 in a storage position of the tubular section 24. The tubular section 24 may have a suitable clamp 28 which prevents passage of urine through the tubular section 24 when the clamp 28 is closed. When it is desired to drain urine from the container chamber 20, the outer end of the tubular section 24 is removed from the pocket 26 and the clamp 28 is opened in order to permit passage of urine through the tubular section 24, after which the clamp 28 is closed and the tubular section 24 is again inserted into the pocket 26 in the storage position of the tubular section 24.

The container 12 may have a hollow connector 30 in the form of a drip chamber attached to the front wall 16 of the container 12 and communicating with the container chamber 20. As shown, the upper portion of the connector 30 is attached to the downstream end of a drainage tube 32, such that the drainage tube 32 communicates with the connector 30. If desired, the connector 30 may have a vent 34 with a bacteria filter of known type to filter bacteria from air passing from the atmosphere into the connector 30 through the vent 34. In use, a catheter (not shown) is passed through the urethra of a patient until the catheter communicates with the patient's bladder, and a proximal end of the catheter extending outside the patient is attached to the upstream end of the drainage tube 32. During catheterization, urine drains through the catheter, drainage tube 32, and the connector 30 into the container chamber 20 for collection therein. Although the described system is closed to the atmosphere, it has been found that bacteria may form in the collected urine in the chamber 20.

The diffusion device 14 comprises an elongated conduit 36 having a lumen 38 extending through the conduit 36, a distal portion 40 located inside the chamber 20 of the receptacle 12, and a proximal portion 42 located outside the receptacle 12, such that the conduit 36 extends through the front wall 16 of the receptacle 12. The conduit 36 may be secured in place to the front wall 16 by a suitable ring 44 of plastic material connected to the front wall 16 and to a central portion of the conduit 36.

The diffusion device 14 also has an inflatable balloon 46 of elastic material secured to a distal end 48 of the conduit 36 in the chamber 20. As shown, the balloon 46 is in the form of a bulb 49 having an annular portion 50 secured to the distal end 48 of the conduit 36. In this configuration, the balloon 46 defines a cavity 52 which communicates with the lumen 38 through an inflation opening 54 at the distal end 48 of the conduit 36. The balloon 46 is constructed from a material which is slightly permeable to passage of liquid over a period of time, such as silicone.

The diffusion device 14 also has valve means 56 of known type secured to a proximal end 58 of the conduit 36, with the valve means 56 communicating with the lumen 38. The valve means 56 may be of the type which is actuated by the tip of a syringe in order to open the valve means, and thus permit pumping of liquid through the valve means 56 into the lumen 38.

In use, the tip of a syringe (not shown) is engaged against the valve means 56 in order to actuate and open the valve means 56, after which an antiseptic agent, such as liquid chlorhexidine or liquid benzalkonium chloride, may be pumped by the syringe through the open valve means 56, the lumen 38, and the inflation opening 54 into the cavity 52 of the balloon 46 in order to inflate the balloon 46. Next, the syringe is removed from the valve means 56 in order to close the valve means in a configuration with the balloon 46 inflated in the receptacle chamber 20. The inflated balloon 46 maintains the antiseptic agent under pressure in the diffusion device 14, and over an extended period of time the antiseptic agent diffuses through the wall of the balloon 46 into the chamber 20 of the receptacle 12 in order to mix with the collected urine. In turn, the antiseptic agent, which mixes with the urine, minimizes the possibility of bacterial growth in the collected urine. In this manner, the diffusion device 14 minimizes the possibility of bacterial growth in the receptacle chamber 20, and thus minimizes the possibility of retrograde bacterial movement from the receptacle chamber 20 toward the patient's bladder, which otherwise could cause deleterious results to the patient.

Figure 3:
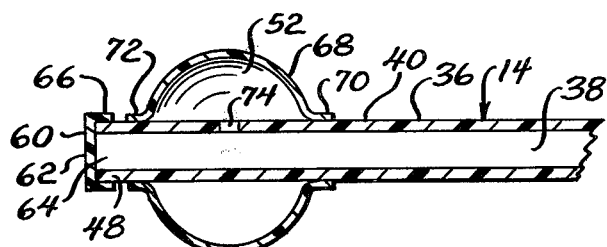
FIG. 3 is a fragmentary sectional view of another embodiment of the diffusion device for the collection device of FIG. 1.

Another embodiment of the diffusion device 14 for the receptacle 12 is illustrated in FIG. 3, in which like reference numerals designate like parts. In this embodiment, the device 14 has a membrane 60 secured to the distal end 48 of the conduit 36 in the receptacle chamber. As shown, the membrane 60 may have a wall 62 which closes an opening 64 in the distal end 48 of the conduit 36, and an annular portion 66 connected to the wall 62 and secured by suitable means, such as adhesive, to the distal end 48 of the conduit 36.

The device 14 of FIG. 3 also has a balloon 68 comprising a sleeve having a proximal end 70 secured in a circumferential zone to the outside of the conduit 36, and a distal end 72 secured in a circumferential zone to the outside of the conduit 36. The proximal and distal sleeve ends 70 and 72 may be secured to the conduit 36 by suitable means, such as adhesive. As shown, the conduit 36 has an opening 74 in a wall of the conduit 36 intermediate the proximal and distal zones 70 and 72 of the balloon 68, and communicating between the lumen 38 and a cavity 52 beneath the balloon 68. The conduit 36 may extend through the front wall 16 of the receptacle 12, and may have valve means of known type secured to a proximal end of the conduit 36, as previously discussed in connection with the device 10 of FIGS. 1 and 2.

In one form, the membrane 60 comprises a material which is slightly permeable to passage of liquid, such as a 0.2 micron filter of polytetrafluroethylene sold by Millipore Corporation of Bedford, Massachusetts, and the balloon 68 may comprise a material impermeable to passage of liquid, such as rubber. In this form, the balloon 68 may be located inside or outside the chamber, as desired. In this form, the syringe is attached to the valve means in order to actuate the valve means, after which the antiseptic agent is pumped through the valve means into the lumen 38 in order to inflate the balloon 68 through the opening 74. Next, the syringe is removed from the valve means in order to close the valve means and maintain the balloon 68 in an inflated configuration. The inflated balloon 68 maintains the liquid antiseptic agent under pressure in the diffusion device 14, and the pressurized liquid slowly diffuses from the lumen 38 through the wall 62 of the membrane 60. In turn, the diffusing liquid mixes with the urine in the receptacle chamber 20, and minimizes the possibility of bacterial growth in the collected urine.

In another form of the device 14 of FIG. 3, the membrane 62 is constructed from a liquid impervious material, such as a suitable plastic, and the balloon 68 is constructed from an elastic material which is slightly permeable to passage of liquid, such as silicone. In this form, the balloon 68 is located in the receptacle chamber 20. In this form, the membrane 60 closes the opening 64 at the distal end 48 of the conduit 36. The antiseptic liquid may be pumped by a syringe through the actuated valve means into the lumen 38 and through the opening 74 into the balloon 68, in order to inflate the balloon 68, as previously described. In this form, the inflated balloon 68 maintains the liquid antiseptic agent under pressure, and the antiseptic agent slowly diffuses through the wall of the inflated balloon 68. Thus, the diffusing liquid mixes with urine in the receptacle chamber 20, and minimizes the possibility of bacterial growth in the chamber 20.

Thus, in accordance with the present invention, the collection device 10 has a diffusion device 14 which permits inflation of a balloon in order to maintain liquid antiseptic agent under pressure. The antiseptic agent diffuses through the balloon or a permeable membrane over an extended period of time, in order to mix the antiseptic agent with collected urine in the receptacle chamber 20, and thus minimize the possibility of bacterial growth in the receptacle chamber 20.

The foregoing detailed description is given for clearness of understanding only, and no unnecessary limitations should be understood therefrom, as modifications will be obvious to those skilled in the art.

I claim:

1. A device for collecting body fluids from a patient, comprising:
    a receptacle having a chamber to receive said body fluids;
    an inflatable balloon of elastic material located in said chamber, said balloon comprising a material which is slightly permeable to liquid; and
    means for establishing communication between said balloon and the outside of said receptacle.

2. The device of claim 1 wherein said balloon comprises silicone.

3. A device for collecting body fluids from a patient, comprising:
    a receptacle having a chamber to receive said body fluids;
    an inflatable balloon of elastic material;
    a membrane in said chamber communicating with the balloon, said membrane comprising a material which is slightly permeable to liquid; and
    means for establishing communication between the outside of said receptacle and said balloon and membrane.

4. The device of claim 3 wherein said membrane comprises polytetrafluroethylene.

5. A device for collecting body fluids from a patient, comprising:
    a receptacle having a chamber to receive said body fluids;
    a conduit having a portion located in said chamber, said conduit having a lumen extending along the conduit and an inflation opening communicating with said lumen; and an inflatable balloon of elastic material secured to said conduit in the chamber and defining a cavity communicating with the inflation opening, said balloon comprising a material slightly permeable to liquid.

6. The device of claim 5 wherein said balloon comprises silicone.

7. The device of claim 5 including valve means communicating with a proximal portion of said lumen.

8. The device of claim 7 wherein said conduit includes a proximal portion located outside said receptacle, with said conduit extending through a wall of said receptacle, and with said valve means secured to a proximal end of said conduit.

9. The device of claim 5 wherein the inflation opening is located at a distal end of the conduit, and in which the balloon comprises a bulb secured to the distal end of the conduit.

10. The device of claim 5 wherein said inflation opening extends through a wall of the conduit, and in which said balloon comprises a sleeve having proximal and distal ends secured to the conduit in spaced circumferential zones, with the inflation opening being located intermediate said zones.

11. The device of claim 5 in which the receptacle has a pair of opposed flexible walls.

12. A device for collecting body fluids from a patient's body, comprising:

a receptacle having a chamber to receive said body fluids;

a conduit having a portion located in said chamber, said conduit having a lumen extending along the conduit, a diffusion opening communicating with said lumen, and an inflation opening communicating with said lumen;

a membrane secured to the conduit in said chamber and closing the diffusion opening, said membrane being slightly permeable to liquid; and an inflatable balloon of elastic material secured to the conduit and defining a cavity communicating with the inflation opening.

13. The device of claim 12 including valve means communicating with a proximal portion of said lumen.

14. The device of claim 13 wherein said conduit includes a proximal portion located outside said receptacle, with said conduit extending through a wall of said receptacle, and with said valve means secured to a proximal end of said conduit.

15. The device of claim 12 wherein the diffusion opening is located at a distal end of the conduit, and in which said membrane is secured to the distal end of the conduit.

16. The device of claim 15 wherein the inflation opening is located proximal the distal end of the conduit in said chamber, and in which the balloon comprises a sleeve having proximal and distal ends secured in circumferential zones to the conduit, with the inflation opening extending through a wall of the conduit intermediate said zones.

17. The device of claim 12 wherein said membrane comprises polytetrafluroethylene.

18. The device of claim 12 in which the receptacle has a pair of opposed flexible walls.

* * * * *